US00PP20209P2

(12) United States Plant Patent
Houser

(10) Patent No.: US PP20,209 P2
(45) Date of Patent: Aug. 11, 2009

(54) ***THUJA OCCIDENTALIS* TREE NAMED 'AMERICAN PILLAR'**

(50) Latin Name: *Thuja Occidentalis*
Varietal Denomination: American Pillar

(76) Inventor: John E. Houser, 106 Village Ct., Woodstock, GA (US) 30188-1917

( * ) Notice: Subject to any disclaimer, the term of this patent is extended or adjusted under 35 U.S.C. 154(b) by 15 days.

(21) Appl. No.: 11/979,597

(22) Filed: Nov. 6, 2007

(51) Int. Cl.
*A01H 7/00* (2006.01)

(52) U.S. Cl. ..... Plt./213
(58) Field of Classification Search ..... Plt./213
See application file for complete search history.

(56) References Cited

U.S. PATENT DOCUMENTS

| | | | |
|---|---|---|---|
| PP2,685 | P | 11/1966 | Moore |
| PP2,861 | P | 2/1969 | Jensen |
| PP3,548 | P | 5/1974 | Cully |
| PP3,551 | P | 5/1974 | Cully |
| PP3,839 | P | 3/1976 | Swane |
| PP5,711 | P | 4/1986 | Sturrock |
| PP8,165 | P | 3/1993 | Hinshaw |
| PP11,217 | P | 2/2000 | Greeves |
| PP11,979 | P2 | 7/2001 | Moon |
| PP12,806 | P2 | 7/2002 | Wilhelmsen et al. |
| PP12,933 | P2 | 9/2002 | Zylstra |
| PP15,850 | P2 | 7/2005 | Yanny |
| PP16,094 | P2 | 11/2005 | Jones |
| PP16,280 | P2 | 2/2006 | Brown |
| PP16,446 | P3 | 4/2006 | Ikuma |
| 2006/0064790 | P1 | 3/2006 | Nemeth |

*Primary Examiner*—Kent L Bell
(74) *Attorney, Agent, or Firm*—Swift Law Office; Stephen Christopher Swift

(57) ABSTRACT

A sport of the 'Hetz Wintergreen' cultivar of *Thuja Occidentalis* tree (commonly known as arborvitae) called "American Pillar". It is nearly twice as dense in its branching habit as the 'Hetz Wintergreen'. It also has a brighter green coloring in the winter. Its increased foliage density makes possible better wind, sight and sound screening with a narrow evergreen hedge. It is reproduced by rootings cut from a parent stock of 'American Pillar'.

7 Drawing Sheets

Latin name of the genus and species of the plant claimed: *Thuja Occidentalis.*
Variety denomination: 'AMERICAN PILLAR'.

BACKGROUND OF THE INVENTION

The invention that is the subject of this application is a new and distinct variety of *Thuja occidentalis* that is fast growing for the species, very narrow, and distinctly different from any other *Thuja occidentalis* known to the inventor in that it is much more compact in its growing habit. This new variety was found growing in the inventor's nursery in Cherokee County, Georgia. It was a naturally occuring branch mutation of one of a number of rooted cuttings of the 'Hetz Wintergreen' variety of *Thuja occidentalis* planted in 1999. In the following six growing seasons, the original plant of this new variety grew to be more than twenty-one feet (seven meters) tall, and slightly more than three feet (one meter) wide.

While this new variety resembles its 'Hetz Wintergreen' parent in growth rate and general shape, its foliage is approximately twice as dense as its parent due to closer internode spacing. Its substantially denser foliage greatly enhances its utility as a screening plant. It is better able than its parent to serve as a windbreak, and as a sight or sound barrier. It surpasses its parent in visual appeal. Its trunk is strictly vertical, and almost always singular, seldom dividing. Its root system is substantial, and well able to sustain the tree against wind damage. Its short lateral side branches make it almost immune to snow and ice. Another distinguishing characteristic is that it maintains a brighter green color in winter than its parent, probably because its denser foliage protects it from the winter sun and wind.

BRIEF SUMMARY OF THE INVENTION

The present invention is a sport of the 'Hetz Wintergreen' cultivar of '*Thuja Occidentalis*' (commonly known as arborvitae) called 'American Pillar'. It is similar to the Hetz Wintergreen in most of its characteristics, but has the following distinguishing traits:

1. It is nearly twice as dense in its branching habit as the 'Hetz Wintergreen'.
2. It has brighter green coloring in the winter.

Its increased foliage density makes it better able to serve as, a windbreak, better able to screen sight and/or sound, and enhances its visual appeal. It is unsurpassed in any landscape requiring screening, especially if space is a consideration, as even a narrow hedge can be an effective screen. It is also useful in landscaping as an exclamation point, or to draw attention to a sign.

'American Pillar' will grow in any reasonable soil. After being established, it can stand as much heat and drought as any arborvitae used as a landscape plant, as it withstood natural conditions in an outdoor nursery without any care. It can survive much more "wet feet" than most plants, as it is native to swamp habitats. (By "wet feet" it is meant that it can survive swampy conditions.) It does best in sun to half shade, but does not do as well in full shade.

'American Pillar' resembles its 'Hetz Wintergreen' parent in that it grows rapidly to twenty-five feet (7.6 meters) or more, and it is a very slender tree, seldom exceeding three feet (one meter) in width at its base, even without shearing. Like its parent, it usually grows only a single trunk, and is very gravity orientated, growing straight up vertically, which assures its resistance to storm damage.

Figure 1:
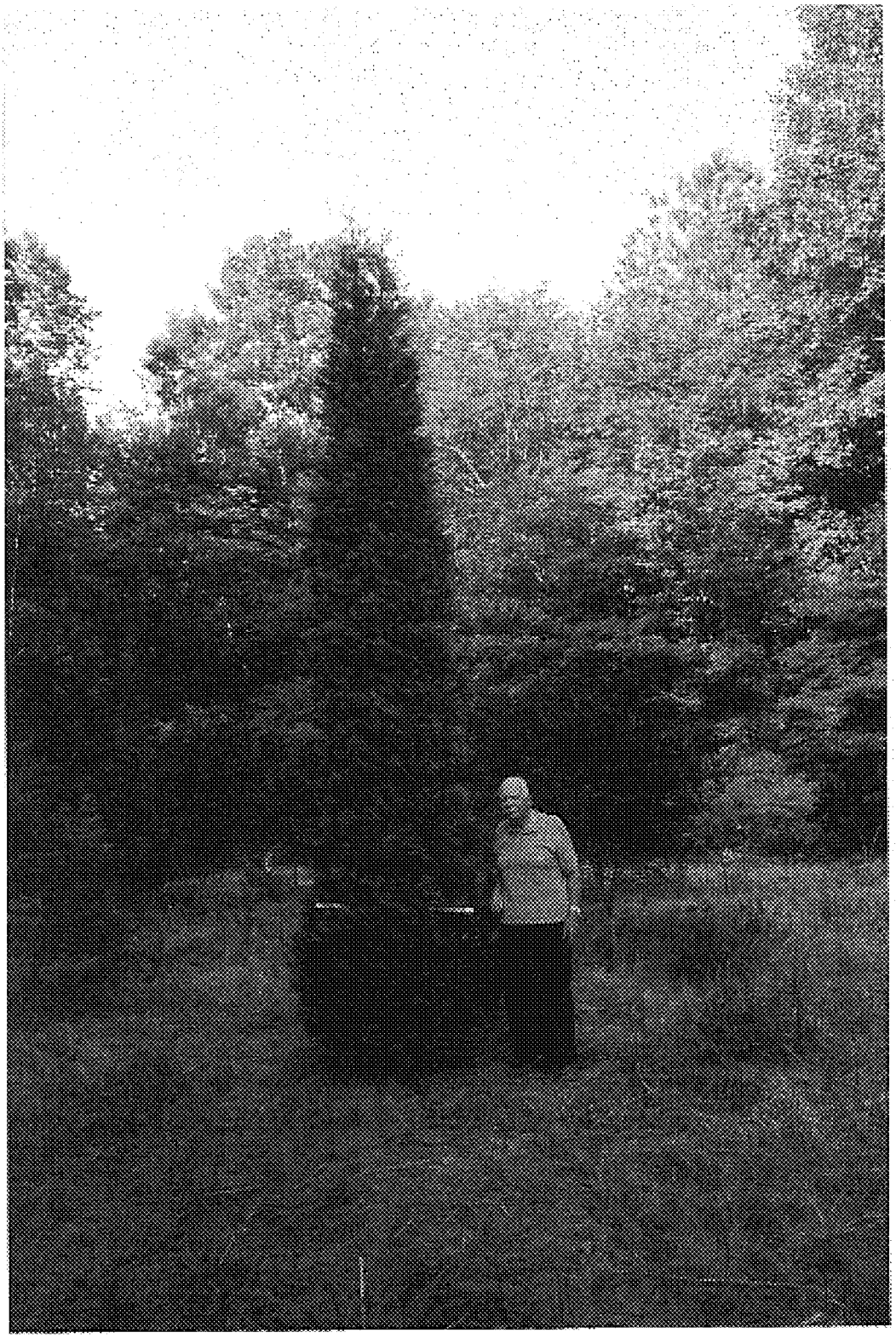
FIG. 1 is a printout of a digital photograph giving an elevational view of a specimen of the 'American Pillar', showing its height and dense foliage. The inventor is shown standing near the tree, and a yardstick is placed in its branches, to show its size.
Figure 2:
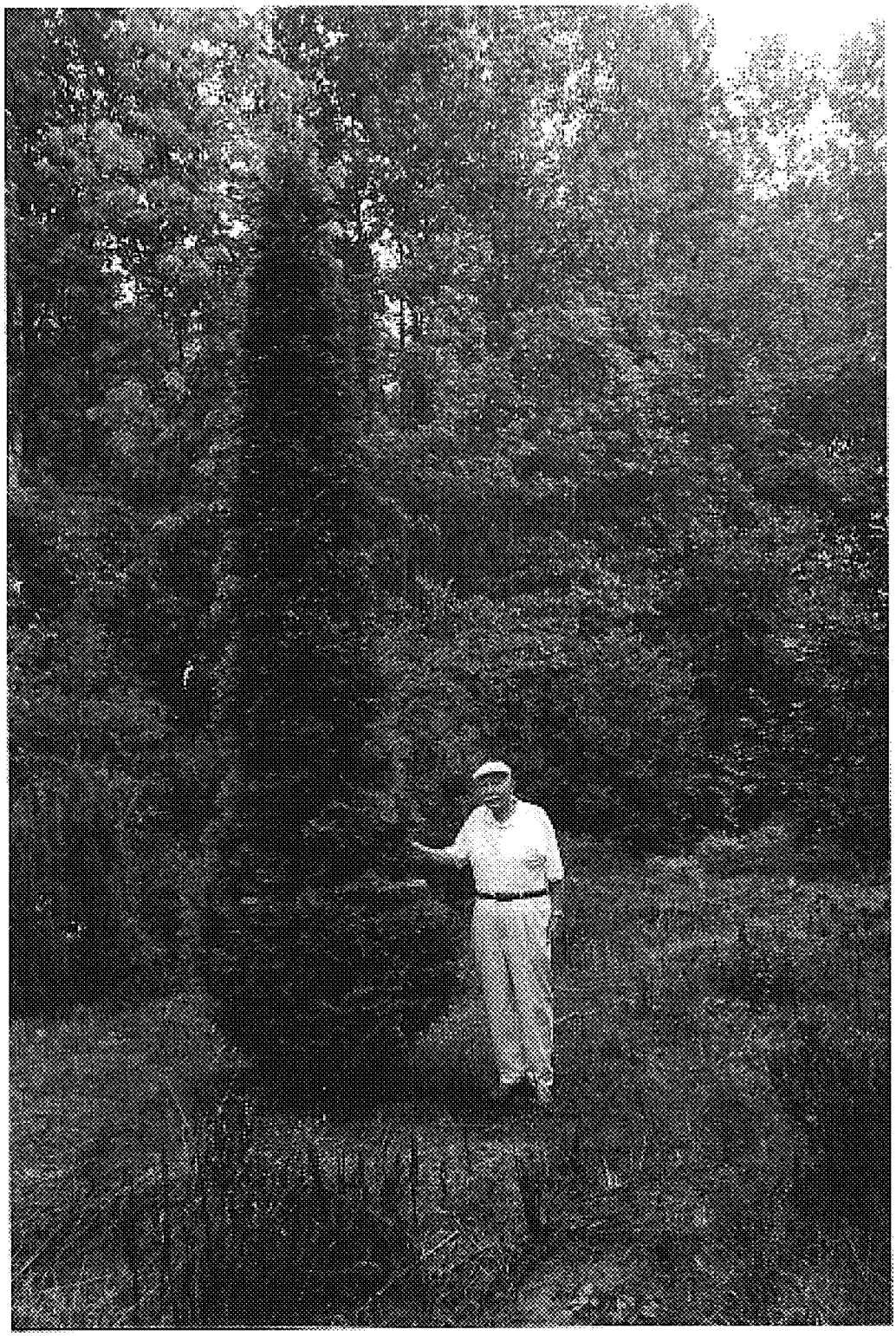
FIG. 2 is a printout of a digital photograph, showing a closer view of the 'American Pillar'.
Figure 3:
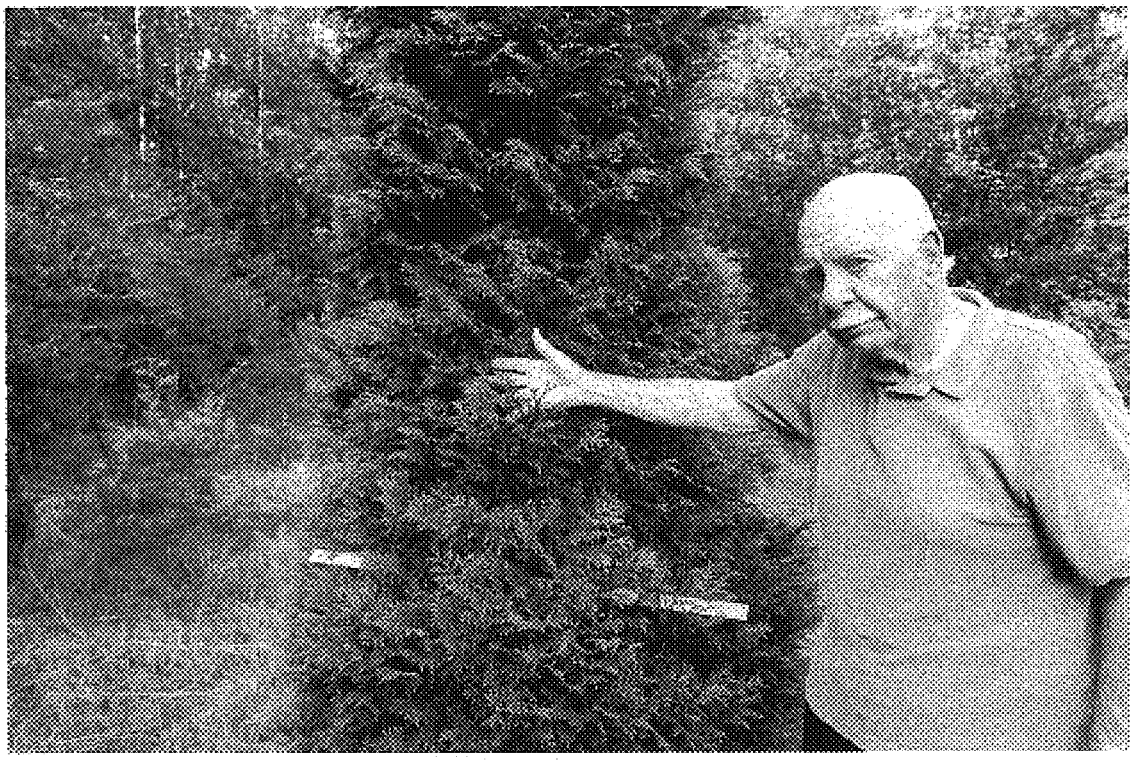
FIG. 3 is a printout of a digital photograph, showing a still closer view of the 'American Pillar'.
Figure 4:
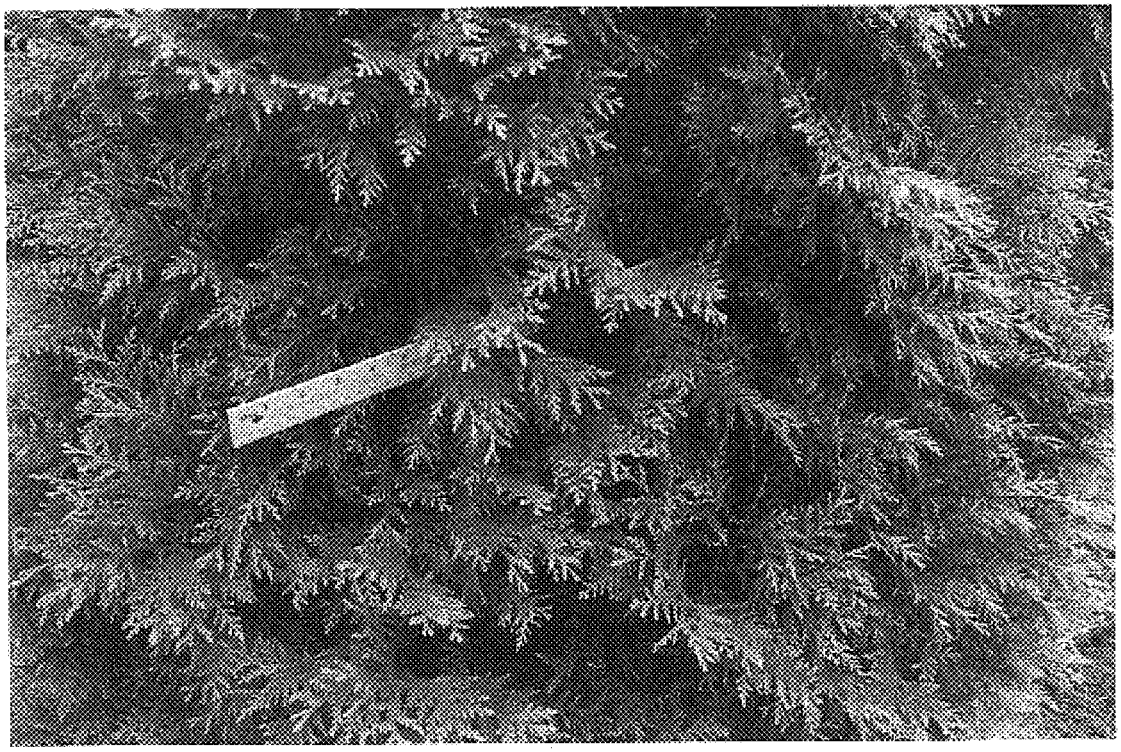
FIG. 4 is a printout of a digital photograph, giving a detail view of the foliage of the 'American Pillar'.
Figure 5:
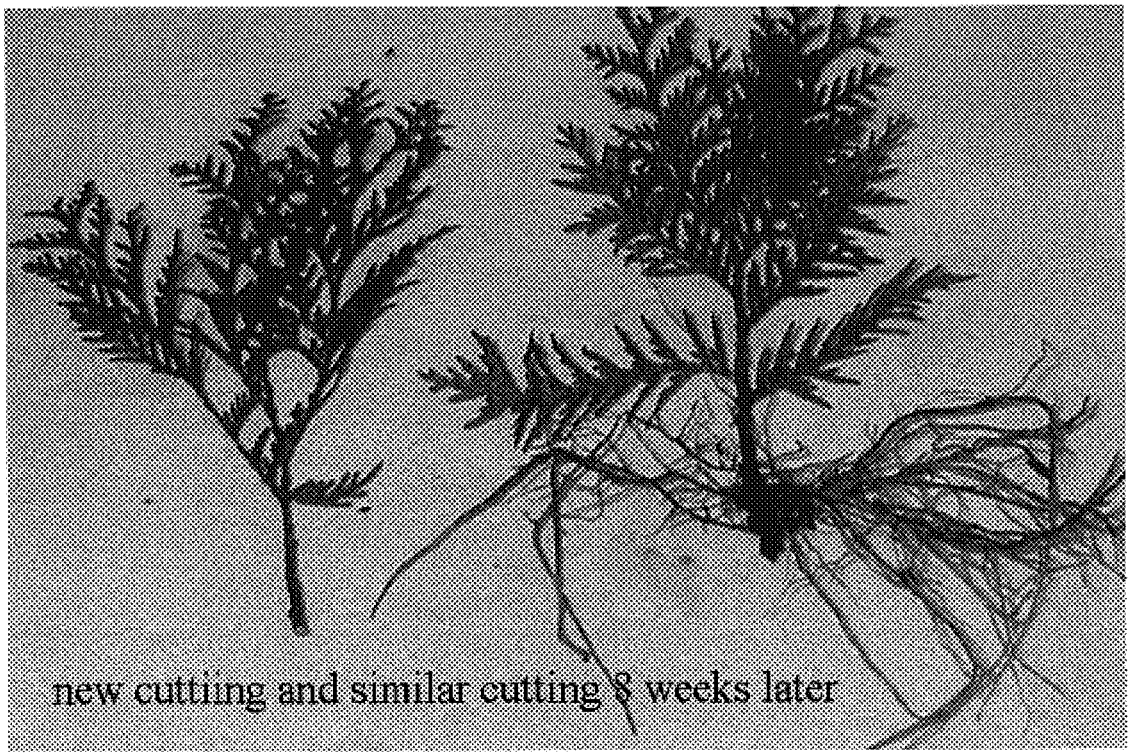
FIG. 5 is a printout of a digital photograph, showing a new cutting from an 'American Pillar' on the left, and a similar cutting from an 'American Pillar' eight weeks after it has been planted, which has been uprooted to show the development of its root structure.
Figure 6:
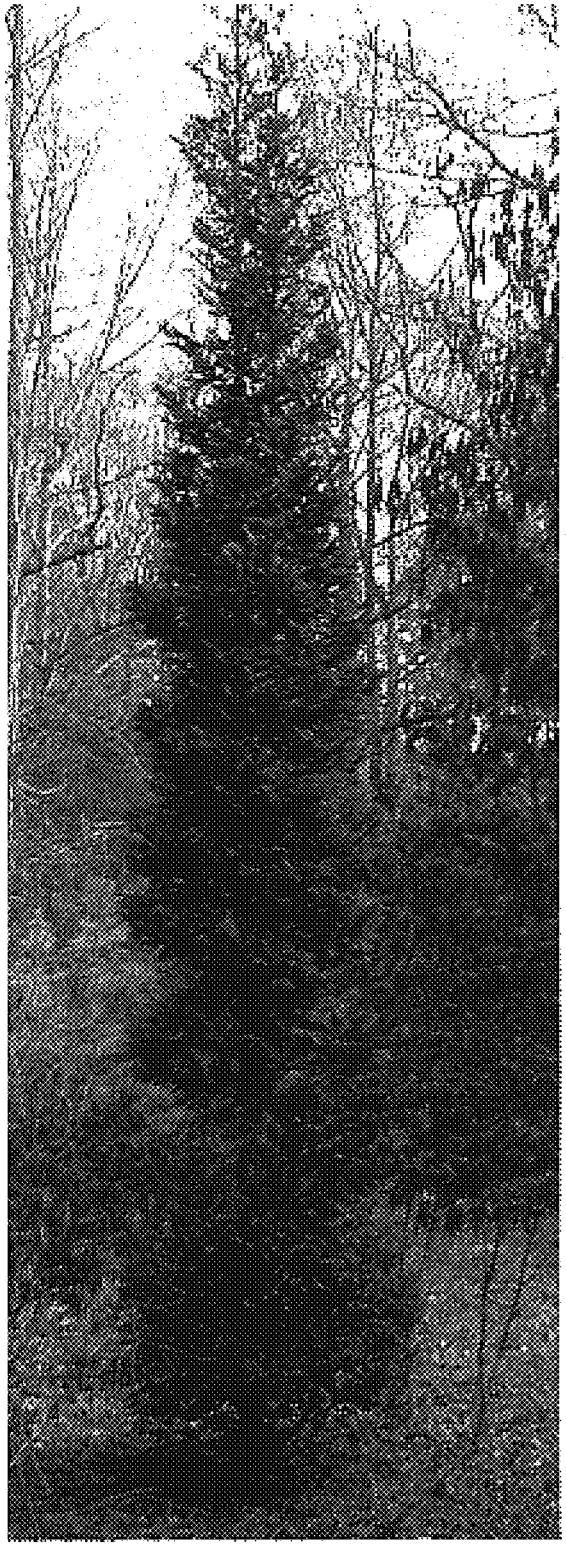
FIG. 6 is a printout of a digital photograph, showing a specimen of the 'Hetz Wintergreen', a variety of *Thuja occidentalis* that is the parent stock of the 'American Pillar'. One can see how much thinner the foliage of the 'Hetz Wintergreen' is compared to the foliage of the 'American Pillar'.
Figure 7:
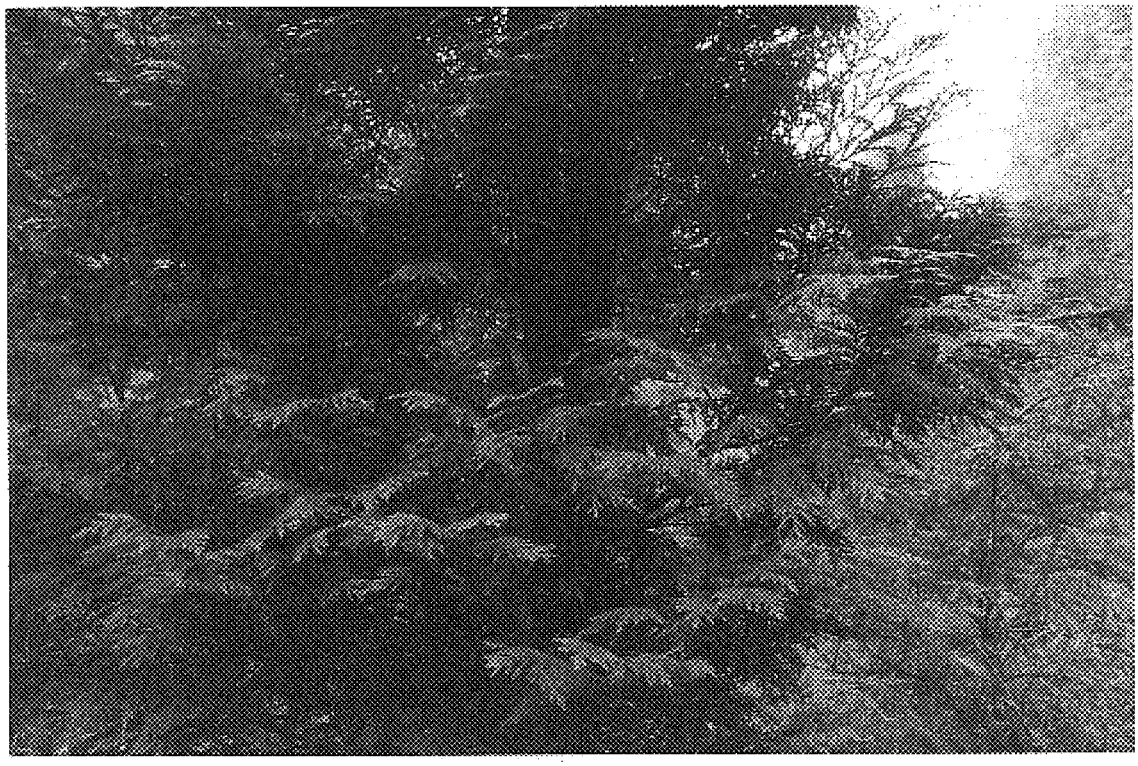
FIG. 7 is a printout of a digital photograph, giving a detail view of the foliage of the 'Hetz Wintergreen'.

The 'American Pillar' plant in FIGS. 1–4 and the 'Hetz Wintergreen' in FIGS. 6 and 7 were in a lot of rooted cuttings, were grown under identical nursery circumstances, individually, and only a few feet apart, and neither was ever trimmed in any way.

DETAILED BOTANICAL DESCRIPTION

Plants used for the aforementioned photographs and the following observations and measurements were grown in Canton, Ga., year round in an outdoor nursery and under conditions which approximate commercial *Thuja production.* Plants had been growing for about seven years when the photographs and description were taken.

In the following description, color references are are made with reference to The Royal Horticulural Society Colour Chart (RHS), 1986 and The PANTONE Book of Color, by Leatrice Eisemer and Lawrence Herbert, published by Harry N. Abrams, Inc., 1990, except where general terms of ordinary dictionary significance are used.

Botanical classification: *Thuja occidentalis* cultivar 'American Pillar'.

Parentage: Naturally-occurring branch mutation of the *Thuja occidentalis* cultivar 'Hetz Wintergreen', not patented.

Propagation:

*Type.*—By cuttings. Cuttings should be from branches and about 15 cm. long (or up to 20 cm. tall). Cut where wood is mature, not from current season's growth.

*Time to initiate roots.*—July or August (in the Northern Hemisphere) or anytime using a heating bed.

*Time to produce a rooted cutting.*—About six to eight weeks during summer months under intermittent mist. A salable plant, 90 cm. to 120 cm. tall, can be produced in two growing seasons from a rooted cutting. They have transplanted readily, with minimal care, when 1.2 meters to 1.5 meters tall, even as bare root plants, when relatively dormant.

*Root description.*—Thick; creamy white RHS 156A, Pantone 12-0817 in color at growing points at ends of roots, light brown RHS 199D, Pantone 17-1134 elsewhere.

*Rooting habit.*—Freely branching; dense.

Plant description:

*Form.*—Narrowly pyramidal evergreen tree.

*Branching habit.*—Freely branching with branches horizontal to arching, branchlets borne in the same plane. Trees maintain their lower branches and foliage to the soil level.

*Plant height.*—About seven meters.

*Plant diameter.*—About one meter.

*Main stem (trunk)description.*—Height: About seven meters. Diameter: About 13 cm. Texture: Woody, smooth. Color: Dark brown RHS 200B, Pantone 19-1322.

*Branch description.*—Length: About 46 cm. Diameter: About 2.5 cm. Texture: Smooth. Color: Dark brown RHS 200B, Pantone 19-1322.

*Branchlet description.*—Length: About 23 cm. Diameter: About 1.2 cm. Texture: Smooth. Color: Varies from light brown RHS 199A, Pantone 17-1430 at base to green RHS 134A, Pantone 18-0527 at the growing tips.

*Leaf description.*—Appearance/arrangement: Flattened and scaled. Length: About 1 to 2 mm. Width: About 0.5 mm. Shape: Lanceolate. Apex: Pointed. Base: Cordate. Margin: Entire. Fragrance: Cedar-like. Color: Developing leaves, upper surface: Light green. Developing leaves, lower surface: Medium green. Fully expanded leaves, upper surface: In full sunlight, Dark green RHS 137A, Pantone 18-0527; in shade, Medium green RHS 137B, Pantone 17-0535. Foliage resistant to sun and winter burning. Fully expanded leaves, lower surface: Dark green RHS 137A, Pantone 18-0527. The foliage of 'American Pillar' is not constant in color, being brighter in summer than in winter. However, it is relatively brighter in winter than 'Hetz Wintergreen'.

Cone description: Small and clustered cones, about 6.3 mm to 9.5 mm in length, and 3 mm to 4 mm in diameter. Cones are green RHS 146C, Pantone 17-0535 when immature, and turn brown RHS 199A, Pantone 19-1322 when they ripen.

Disease/pest resistence: Plants of the new *Thuja* are resistant to most pathogens and pests common to *Thujas*.

Weather tolerance: Plants of the new *Thuja* have been observed to be tolerant to drought, rain, wind and temperatures ranging from −32° C. to 40° C.

Range: Hardiness zones 5 through 8.

It is claimed:

1. A new and distinct variety of *Thuja occidentalis tree,* named 'American Pillar', substantially as illustrated and described herein.

* * * * *